United States Patent [19]

Cushman

[11] 4,176,278
[45] Nov. 27, 1979

[54] PANORAMIC DENTAL RADIOGRAPHY EMPLOYING INTRAORAL RADIATION SOURCE AND IMAGE INTENSIFYING MEANS

[75] Inventor: Robert H. Cushman, Princeton, N.J.

[73] Assignee: Pennwalt Corporation, Philadelphia, Pa.

[21] Appl. No.: 955,999

[22] Filed: Oct. 30, 1978

[51] Int. Cl.² ............... G01N 21/00; G01N 23/00; G21K 5/06; G21K 5/08
[52] U.S. Cl. .................. 250/439 P; 250/490; 250/323; 250/320; 250/523
[58] Field of Search ............ 250/439 P, 439 R, 490, 250/523, 320, 323

[56] References Cited

U.S. PATENT DOCUMENTS

| | | | |
|---|---|---|---|
| 2,798,958 | 7/1957 | Hudson et al. | 250/439 P |
| 2,976,416 | 3/1961 | Ellman | 250/439 P |
| 3,045,118 | 7/1962 | Hallman et al. | 250/439 P |
| 3,636,349 | 1/1972 | Faude et al. | 250/439 P |

Primary Examiner—Craig E. Church
Assistant Examiner—Thomas P. O'Hare

[57] ABSTRACT

Radiation from an intraoral source which travels arcuately within the patient's oral cavity is collimated with camera slot of a panoramic dental X-ray machine to thus obviate the need for the X-ray tube head and shifting of the patient.

12 Claims, 8 Drawing Figures

PANORAMIC DENTAL RADIOGRAPHY EMPLOYING INTRAORAL RADIATION SOURCE AND IMAGE INTENSIFYING MEANS

STATEMENT OF THE INVENTION

The present invention relates to radiography and more particularly to intraoral radiation means for providing panoramic radiographs of dental arch structures.

CROSS-REFERENCE TO OTHER APPLICATIONS

Reference is hereby made to copending patent application Ser. No. 926,175, filed July 20, 1978, for "Panoramic Dental X-Ray Machine Employing Image Intensifying Means," of R. H. Cushman, assigned to the present assignee.

BACKGROUND AND SUMMARY OF THE INVENTION

Prior art panoramic dental X-ray machines are well known. Some provide a continuous image of the dental arch area and commonly employ an X-ray source and X-ray film both optically aligned with each other and supported on a rotatable carrying arm which orbits a patient situated in the path of the X-ray beams. The patient may remain stationary or be transported in a patient chair in accordance with various type drive mechanisms in order to simulate the generally elliptical shape of the human dental arch. The continuous image radiograph provides the dentist with a panoramic view of the teeth and associated structures and is therefore a useful diagnostic aid in many phases of dental practice.

Various other prior art apparatus provide a discontinuous, or split image panoramic radiograph which possesses certain advantages. Here, the dentist is presented with additional interpretive information since two distinctly different views of the incisors, or centrals area are provided. Additionally, overlying spinal shadow which would be cast over the central-bicuspid region are eliminated since X-rays are not generated when the spine is aligned with the X-ray source and film.

Regardless of the type radiographic image to be obtained, i.e., continuous or discontinuous, compensation is usually made for the fact that the curvature of the desired area of focus is generally not a true circle or ellipse. Thus, the rate of film travel must be varied in accordance with the rate of travel of the X-ray source about the patient's head in order that the radiological projections occupy a distance on the film equal to the linear distance of a curved structure being X-rayed, such as a typical dental arch.

In U.S. Pat. No. 2,798,958, apparatus is disclosed for varying the rate of film travel relative to the rate of travel of the X-ray source. The X-ray source and film carrier are both supported by a single member permitting both the X-ray source and film carrier to orbit the patient at an uniform rate of travel. Means are also disclosed for reorienting the patient after completion of one-half of the excursion cycle in order to relocate the center of the axis of rotation with respect to the patient's head prior to X-raying the other one-half of the dental arch in order to provide the discontinuous, or split radiographic images.

In U.S. Pat. No. 3,045,118, apparatus is disclosed which automatically shifts the patient in order that the line of sight between the X-ray source and film bypasses the patient's spinal column and permits X-raying of the other half of the dental arch. Apparatus is also disclosed therein for continuously moving an X-ray source and extraoral film holder about the patient.

In U.S. Pat. No. 3,636,349, structure is disclosed for revolving the X-ray source and film carrier about the head of a patient who remains fixed in position while the centerline of the orbit continuously moves through an arcuate path approximating the arch of the patient's teeth. The patent further discloses film carrier means which may be used advantageously in the practice of the present invention.

Thus, the prior art discloses various types of structures, apparatus and mechanisms for orbiting the X-ray source-X-ray film (tube-head-camera) assemblies in circular or arcuate paths; for varying film travel speed in accordance with tubehead-camera assembly movements; for shifting the patient in a chair; and for providing continuous or discontinuous type radiographic images.

In each of the aforedescribed prior art systems, the patient is subjected to radiation doses of sufficiently high intensity in order to project the desired images adequately onto the X-ray film. The presence of a large X-ray tubehead was necessary, including means to power and control it. Further, the chair carrying the patient was often-times shifted at an appropriate moment in order to bypass the spinal column; and/or the tubehead-camera assembly was caused to describe an arcuate path in an attempt to duplicate the shape of a typical dental arch.

The present invention will be described hereinafter substantially in conjunction with an intraoral radioactive point source, but it is intended to embrace intraoral X-ray sources as well.

The present invention eliminates the need for (a) X-ray tubehead and means to power and control it, (b) chair shift, and (c) non-circular path of the camera assembly. An intraoral radioactive point source is herein provided which coacts with a circularly orbiting camera assembly such that radiation emanating from the radiation point source and passing through the patient's dental arch structures is automatically continuously collimated with a slit diaphragm, or slot, disposed in a central forward portion of the camera assembly. The radioactive point source is enclosed within a shielded container having an axis of rotation which is not a fixed point within the patient's mouth, but where the axis of rotation is continuously moved along a predetermined horizontal arc within the mouth to thus provide undistorted images of dental arch structures. The radiation entering the camera slot may then be received by an image intensifying device secured within the camera assembly, and the output from the image intensifier activates light-sensitive film for producing the full size panoramic radiograph. In lieu of, or addition to the radiograph, an electronic display of the images may readily be obtained if desired.

The present invention does not require the presence of an image intensifying device. That is, conventional X-ray film with intensifying screens may be used advantageously wherein the intraoral X-ray source may be a rod anode which is conveniently disposed in an X-ray transparent wedge-shaped bite block, for example.

Additional advantages, among others, to be derived from practicing the present invention are reduced radiation dosage to the patient and sharper images on the radiograph due to an absence of interfering structures between the radiation source and dental arch compared to extraoral source systems. By controllably moving the radiation source within the mouth of the patient along a predetermined horizontal arc, described later, a more favorable geometry of source-to-patient-to-camera is realized for decreasing overlap of adjacent teeth to provide more valuable diagnostic information, for example, of caries between adjacent teeth. Further, small segments of the dental arch may be scanned to efficiently perform periapical and bite-wing functions with different geometry and magnifications. Still further, radiographing of the entire dental arch structure with only a single scan may be achieved, as opposed to known prior art methods which require two separate views of the dental arch, each view or scan being made from a different fixed point and where the film is stationary. It is understood, of course, that two or more scans may be utilized as an alternative.

DETAILED DESCRIPTION OF THE INVENTION

Figure 1:
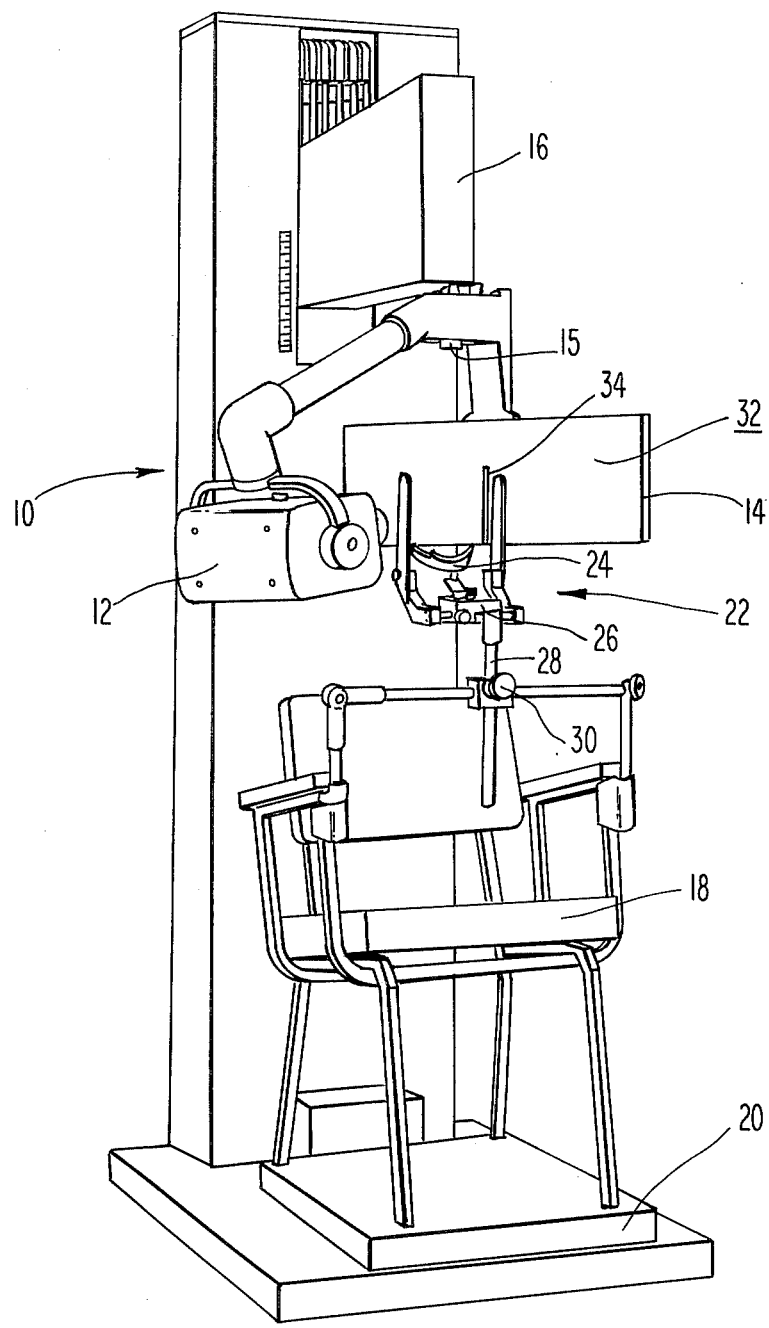
FIG. 1 is a perspective view of a prior art panoramic dental X-ray machine.

In FIG. 1, a typical prior art panoramic dental X-ray machine 10 of the assignee includes a tubehead 12 and camera 14, or film holder assembly, which carries film to be activated by an X-ray source within tubehead 12. Tubehead 12 and camera 14 rotate as a unit with rotating shaft 15 which depends from a counterbalanced vertically adjustable horizontal shroud assembly 16.

A chair 18 is mounted on a base 20 which causes the chair to be shifted at a predetermined moment during the panoramic radiographing of the patient's dental arch area. Chair 18 supports a chin rest assembly 22 which includes a chin rest 24, chin rest mounting block 26, a chin rest assembly adjustment rod 28 which permits vertical adjustment of the chin rest assembly 22 through a chin rest assembly vertical adjustment knob 30. Camera 14 includes a front panel 32 which is provided with a slit diaphragm or slot 34 centrally thereof.

Figure 2:
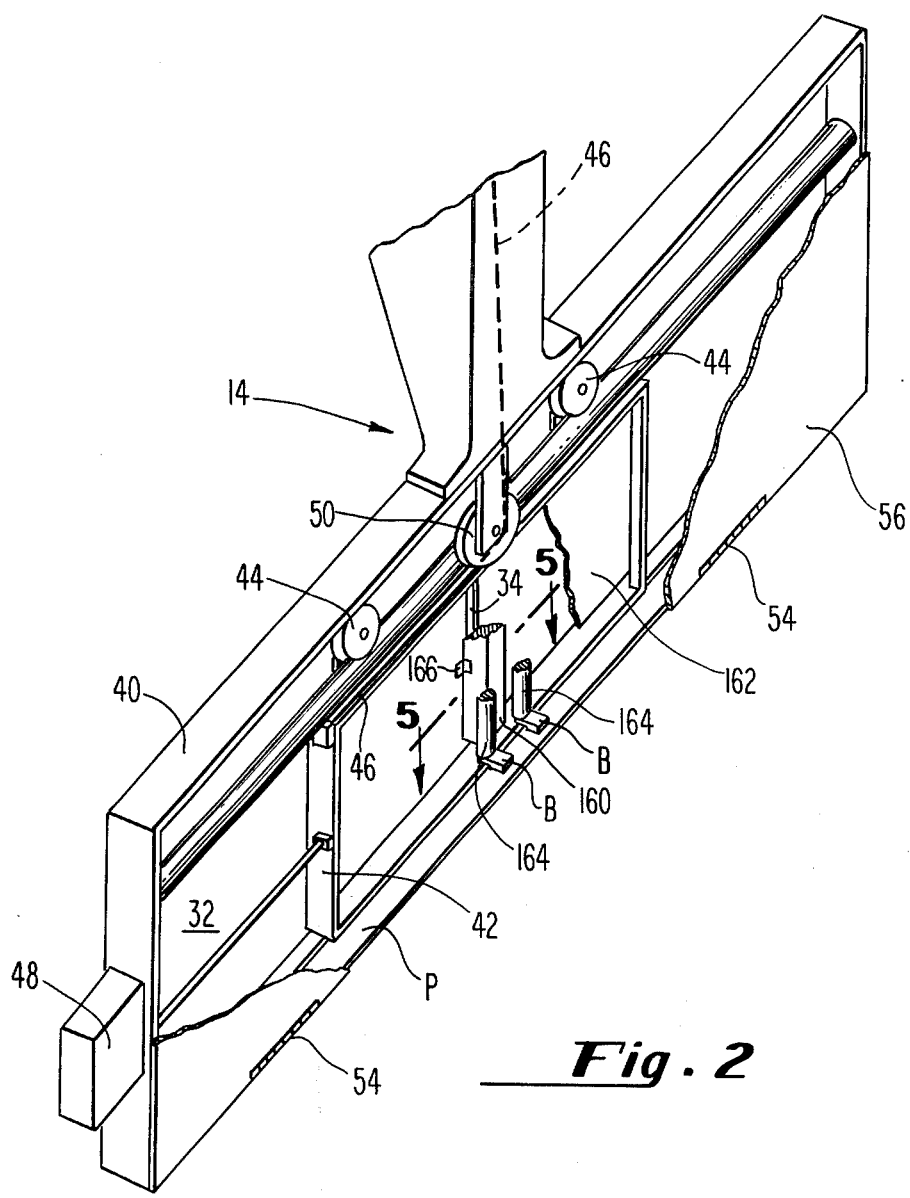
FIG. 2 is a perspective view of camera (film holder) assembly of FIG. 1 modified to include an image intensifying device positioned for use therewith.

The camera or film holder assembly 14 is conventional, except as modified, later described. It comprises film holder 40 (FIG. 2), film carriage 42 which travels within the film holder along rollers 44 when cable 46 and retrieving spring 48 cooperate, through cable roller 50 and other means, to move film carriage 42 and its film past slot 34. Slot 34, of course, permits X-rays from the X-ray source within tubehead 12 to pass through slot 34 for activation of the film, and prevents scatter radiation from entering the camera assembly to cause image deterioration. Hinges 54 permit door 56 to be opened for gaining access to the interior of film holder assembly 14. Door 56 is provided with a lead shield (not shown) aligned with tubehead 12 and slot 34.

Cable 46 communicates with suitable structure for controlling the rate of travel of film carriage 42 independently of the speed of rotation of the tubehead-camera assembly. Specific means for controlling rate of film travel speed as well as means for effecting rotation of the tubehead-camera assembly form no part of the present invention. Reference however is again made to the aforementioned U.S. patents for disclosing and teaching such means. Reference is also made to the cross-referenced related patent application.

An image intensifying device 160, light-sensitive film 162, and film guide roller assemblies 164, modify the structure of conventional film holder assembly 14. Image intensifier 160, in a suitable vacuum envelope, is aligned with slot 34 and is secured thereagainst within the film holder assembly by suitable means, such as brackets 166. The illustrated image intensifier will have nominal dimensions of $5\frac{1}{2}''\times \frac{1}{2}''\times \frac{3}{8}''$, the $5\frac{1}{2}''\times \frac{3}{8}''$ dimension defining an input face which opposes the nominal $5\frac{1}{2}''\times 17/64''$ opening of slot 34 of the camera or film holder assembly 14.

Film guide roller assemblies 164 are rotatably mounted on brackets B, secured to bottom plate P of film holder assembly 14. Means for adjusting the film guide roller assemblies in order to accommodate image intensifiers of varying depths are known and are not disclosed or illustrated herein. Although only one roller guide for each film guide roller assembly 164 is shown, it is understood that a pair of cooperating rollers for each such assembly may be used, if desired. Alternatively, the film guide roller assemblies may be mounted to door 56.

The present invention may be used advantageously with the panoramic dental X-ray machine illustrated in FIG. 1. Of course, the presence of tubehead 12 will no longer be necessary. For purpose of maintaining balance however of the film holder assembly, a weight may be substituted in a suitable location for the removed tubehead. The present invention is also usable with other type panoramic dental X-ray machines, such, for example, as where the camera (and tubehead, although no longer necessary) is mounted on a vertical pedestal which orbits the camera about the head of the seated patient.

Figure 3:
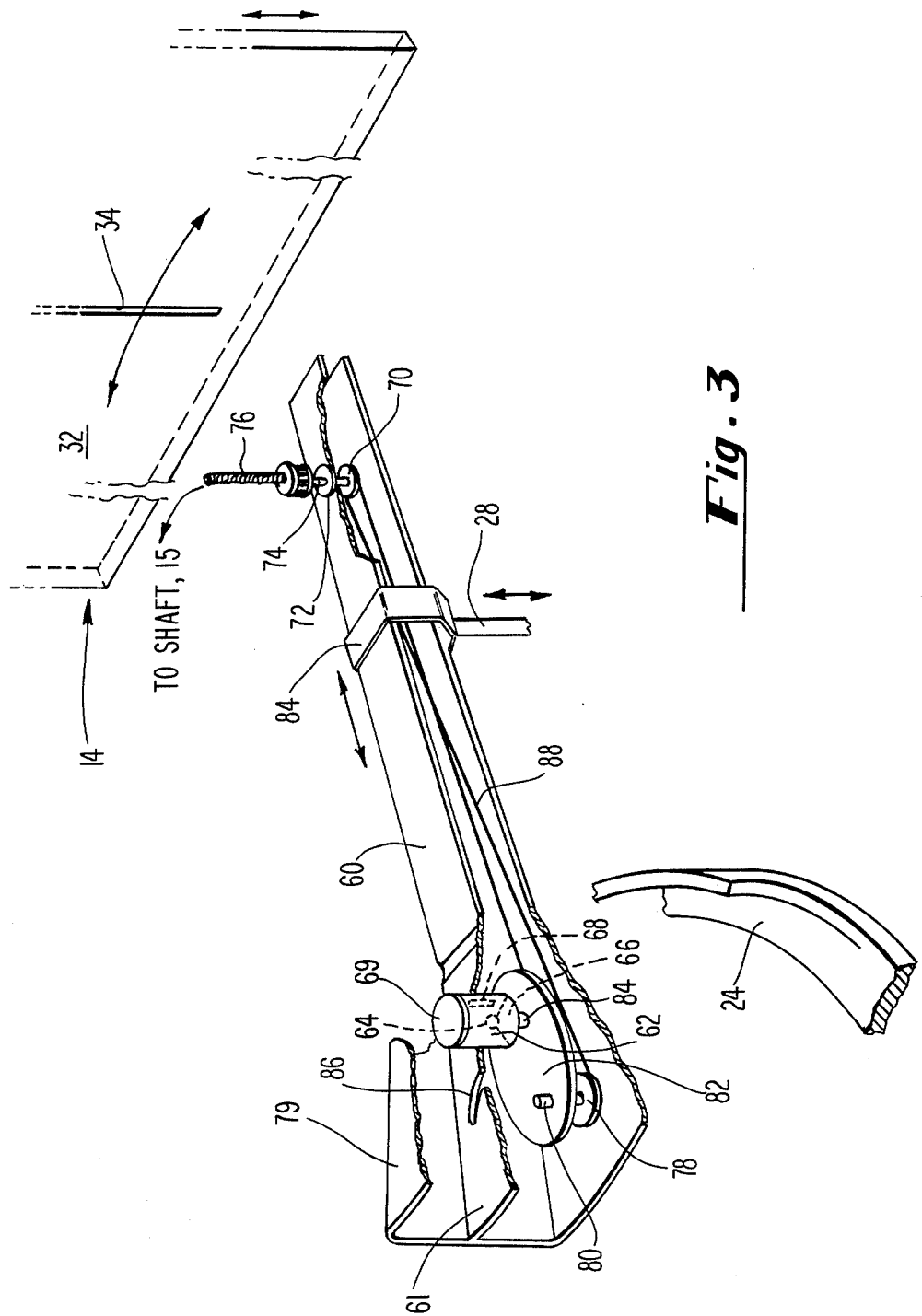
FIG. 3 is a perspective view, partially cutaway, of an embodiment of the present invention adapted for use with the machine of FIG. 1.

In FIG. 3, a C-shaped bar 60 has a hollow bite block or flared portion 61 for insertion into the mouth of the patient, which flared portion rotatably mounts a cylindrical shielded container 62, on lever arm 82, the shielded container containing a radioactive point source 64 at an apex portion of an inverted cone support member 66. Shielded container 62 is provided with a slit 68 for permitting passage of radiation therethrough generated by the radioactive source 64.

Container 62 is made of lead and is coated with a suitable plastic material. Container 62 has a threaded lid 69, of similar material, which may be removed for gaining access within the container. The other end of bar 60 includes a pulley member 70 mounted for rotation therewithin by known means, such, for example, as bearings 72. Pulley member 70 is provided with an upwardly extending shaft 74 to which one end of a flexible shaft 76 is coupled, the other end being connected to shaft 15 which causes camera 14 to orbit the patient. Flexible shafts are well known. They comprise basic elements of power transmission and are designed to transmit power or control from a driving element, such as shaft 15, to an element to be driven, in this instance, shaft 74. Means for coupling flexible shaft 76 to the driven and driving elements are conventional and are not detailed herein.

Another pulley member 78 is similarly rotatably mounted within the hollow bite block or flared portion 61 by shaft 80. Lever arm 82 is secured to shaft 80 within flared portion 61, arm 82 rotating in response to rotation of shaft 80. Lever arm 82 is provided with an upstanding pin 84 which extends through, and is slidable within a curved slideway 86 provided in flared portion 61. Pin 84 mounts shielded container 62 such that rotation of pulley 78 causes a similar rotation of lever arm 82 which effects movement of container 62 along a predetermined path or arc coinciding with slideway 86. Slit 68 remains in constant collimation with slot 34 of camera 14. Thus, flexible shaft 76, in response to slow orbiting movement of shaft 15, causes shaft 74 to rotate accordingly which causes pulley 70 to similarly rotate, which, in turn, causes pulley 78 to rotate in an opposite direction by means of a crossed wire loop 88 articulating therebetween. Since horizontal movement of container 62 within the patient's mouth may cause contact between the container and the roof of the mouth to thereby elicit an unwanted gagging response, a removable cover 79 is provided over flared portion 61 to thus enable container 62 to move freely within slideway 86. Cover 79 is secured in place by any conventional means.

The center of rotation of camera 14 is situated approximately at the radioactive source. If pulleys 70 and 78 are of equal dimensions, it is apparent they will rotate in unison, but in opposing directions during a typical panoramic scan and collimation between slit 68 and slot 34 will be maintained.

Flared portion or bite block 61, cover 79, and container 62 are placed in the mouth of the patient, the chin of the patient resting firmly in chin rest 24. Bar 60 is vertically adjustable through chin rest assembly adjustment rod 28 and chin rest assembly vertical adjustment knob 30, the former being attached to a bracket member 84 which supports bar 60 and yet permits its horizontal movement for adjustment purposes within the patient's mouth.

It is understood that the invention is not intended to be limited to the aforedescribed structure. For example, appropriate clock and watch gearwork type mechanisms may be used; basic mechanical movements providing the proper collimation, and the like.

Figure 4A:
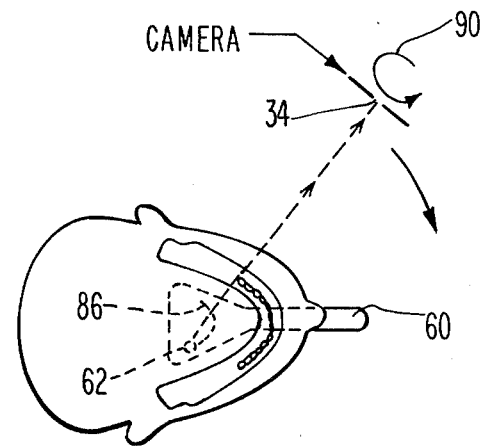
FIGS. 4A, 4B and 4C are diagrammatic views illustrating relative locations of various elements associated with the invention in several positions of a typical panoramic scan.
Figure 4B:
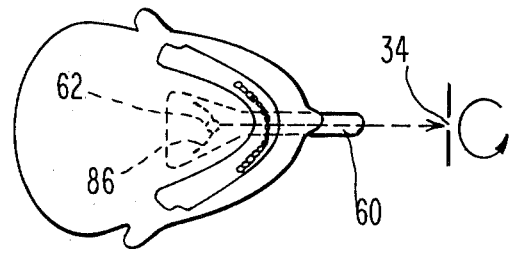
Figure 4C:
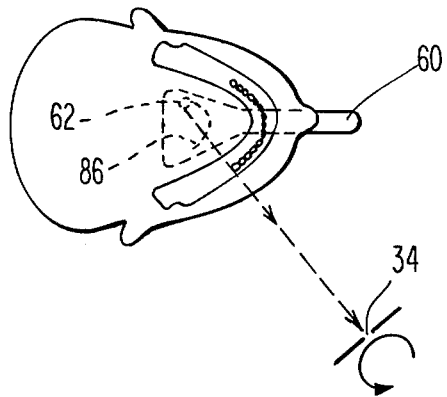

Reference is now made to FIGS. 4A, 4B and 4C, wherein a camera is shown in three successive positions of clockwise orbit about the patient while film 90 travels in an opposite direction. Film 90 is illustrated as a circular type within a circular type camera, it being understood of course, that flat type film, such as film 162, in camera 14, shown in FIG. 2 would be equally operable. Radioactive source 64 within shielded container 62 is generating radiations which leave slit 68 and enter slot 34 of the moving camera.

In FIG. 4A, the left molar area of the patient is being radiographed. As the camera approaches mid-position, or when the centrals or incisors are being radiographed (FIG. 4B), container 62 will be approximately mid-position within slideway 86 by virtue of lever arm 82 rotating in accordance with rotation of shaft 80 secured to pulley 78. In FIG. 4C, the right molar area is being radiographed, the apparatus illustrated being substantially a mirror image of that shown in FIG. 4A, and container 62 will have traveled to the other end of slideway 86.

Alignment of the two pulleys before commencing radiographing in order to provide the proper collimation is facilitated by ready access within bar 60 through its open side. Bar 60 is ideally no thicker than about $\frac{1}{4}''$ deep and about $\frac{1}{2}-\frac{3}{4}''$ wide. Shielded container 62 will have a diameter approximately the width of bar 60. Cover 79 will have no sharp edges and will have dimensions only large enough to permit arcuate movement of container 62 within slideway 86.

Radioactive source 64 is desirably no larger than about 0.1 mm in diameter. Slit 68 will have a length slightly in excess of the length necessary to permit the entire length of camera slot 34 to receive the radiation from radioactive point source 64, which radiation, of course, travels in a straight line. Width of slit 68 is determined by the focal trough desired, i.e., a narrow slit provides a wider focal trough. However, a wider focal trough requires a more intense beam of radiation, or a longer exposure to the radiation by the patient.

Other methods of slit-to-slot coupling to insure collimation therebetween may be provided by magnetic coupling means, gearing, and the like.

Some representative radioactive sources are iodine 125, iron 55, and americium 241.

Shielded container 62 may be caused to travel a non-circular horizontal path within the mouth of the patient in order to obtain specific geometric details of certain structures within the dental arch-temporomandibular joint area. Such non-circular movement of container 62 is contemplated by the principles herein disclosed.

Figure 5:
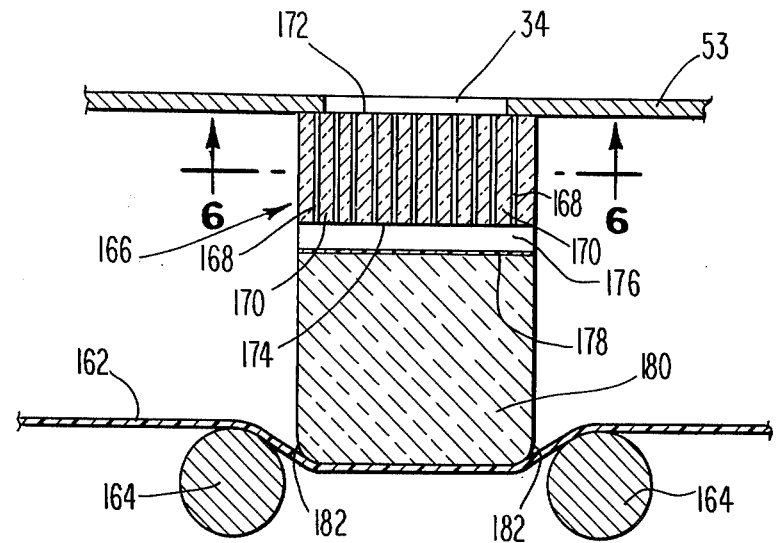
FIG. 5 is a sectional view of the image intensifying device of FIG. 2 taken along line 5—5 thereof.
Figure 6:
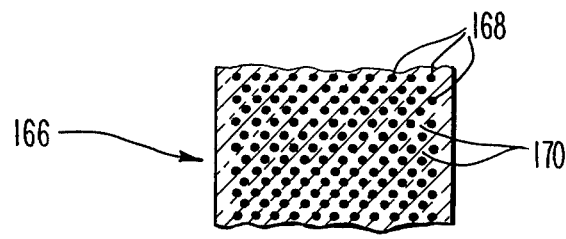
FIG. 6 is a section of the microchannel plate of the image intensifying device of FIG. 5 taken along line 6—6 thereof.

Referring now to FIGS. 5 and 6, radiation from the radioactive source passes through slot 34 of the camera to strike the input face 172 of a lead glass microchannel plate 166 of image intensifying device 160, the microchannel plate 166 comprising an array of spaced parallel microchannels 168 aligned substantially with the direction of travel of the radiation. Microchannels 168 are hollow glass cylinders with a known resistive secondary-emission coating disposed on their interior surfaces. Interstices 170, separating the microchannels from each other, comprise a lead glass which converts the radiation from the radioactive source to electrons via bombardment of the lead ions in the glass by the radiation. The microchannels are electrically connected in parallel by means of a metallic film of chromium disposed on input face 172 and output face 174 of the microchannel plate 166. Alternatively the input face 172 may be coated with a suitable conversion coating to convert the radiation to electrons. When a potential is applied between these faces by conventional means, an uniform axial electrostatic field is generated in each of the microchannels. Thus, an electron entering a microchannel adjacent the input end of microchannel plate 166 will be vastly multiplied in number before exiting at output face 174 due to cascading action wherein primary electrons, initially formed by the aforementioned bombardment, collide with the secondary-emission coating material to cause secondary electrons to be emitted. These secondary electrons now assume the role of primary electrons for the next collision further down the microchannel, and so on.

A typical gain of $10^3$ electrons is realized by means of microchannel plate 166, although gains in the millions are readily currently achievable. It is appreciated that other image intensifier techniques which will convert the radiation to electrons, multiply them, and then provide an amplified light output may be used advantageously with the present invention. In some cases, the efficient conversion of the radiation to light by microchannel plate structures without amplification may also be used advantageously with the present invention.

Typically, microchannel 168 is about 12 microns in diameter.

The microchannels have a center-to-center spacing of about 15 microns. Since microchannel plate 166 is approximately ⅛" in thickness, the length-to-diameter ratio of each microchannel is about 250.

The multiplied electrons leaving output face 174 are accelerated by about 5 kV across a gap 176 of about 0.05". The accelerated electrons are caused to impinge on a phosphor screen 178 disposed on the input side of a fiber optic face plate 180. Phosphor screen 178 converts the electrons to photons which are transmitted through fiber optic face plate 180 to thereby activate the fast light-sensitive film 162. Film 162 comprises a single or double emulsion layer having a conventional backing plate, an emulsion layer facing the image intensifier. Intensifying screens used with conventional X-ray equipment are not required in the practice of the present invention.

The resultant intensified image may have static and dynamic resolutions exceeding 10 and 7 line pairs/mm respectively. The radiation dosage to the patient is reduced by about 10 to 1. Experiments have confirmed 40 to 1 dosage reductions but with some increase in noise level. Optimum results for any specific application therefore requires balancing dose reduction and noise. As aforementioned, electron gain, and hence dose reduction, may be achieved by adjusting potential applied to the image intensifier.

Means are known for applying a potential across input face 172 and output face 174 of the microchannel plate; for providing a sufficient voltage across gap 176 to accelerate the multiplied electrons from microchannel plate 166 to phosphor screen 178; and for vacuum sealing the entire image intensifying device 160 for proper operation thereof.

Image intensifier 160 has an indicated depth of about ½" which may readily be changed by simply increasing or decreasing the depth of fiber optic face plate 180. The nominal ½" depth of image intensifier 160 is accommodative to the existing film holder assembly 14 without requiring unnecessary modifications thereto. Film guide roller assemblies 164 permit film 162 to travel unimpeded in constant low pressure contact relationship across the output face of fiber optic face plate 180.

Output face of fiber optic face plate 180 is provided with small radii 182 in order to prevent possible damage to film 162 as it lightly slides thereacross. Although film 162 will, ideally, contact the output face of fiber optic plate 180, photon image scatter is within tolerable limits if distance between film 162 and output face of face plate 180 is maintained less than about 0.005".

It is understood of course that the individual fibers comprising fiber optic face plate 180 are substantially aligned in the same direction as microchannels 168.

The invention is not intended to be limited to the image intensifying device shown and described. For example, X-ray detection or image intensifying devices employing scintillators, photocathodes, aluminized phosphor screens, electronic multiplier arrays of various types, etc. may be used advantageously with the present invention, with or without adaptation.

An embodiment of the invention constructed in accordance with the principles herein disclosed utilized the following, dimensions being approximate:

Radioactive source 64: Iodine 125, 0.09 mm diameter
Shielded container 62: ¾" diameter ×⅝" high
Slot 68: ⅛" long×1/32" wide
Bar 60: ¾" long×⅜" deep
Radioactive source 64 to teeth: 3 cm
Pulleys 70 and 78: ¼" deep, 1.6" circumference
Wire 88: 0.008" nichrome
Camera 14: orbits about 11° per second
Flared portion 61 and cover 79: sufficiently small to fit within mouth.

I claim:

1. In a machine for providing panoramic radiographs of dental arch structures of a patient seated in a chair which includes a cooperating chin rest assembly for maintaining head of said patient in a secured position and wherein a film holder assembly is provided with a slot in a front panel thereof, said slot being capable of permitting radiation passing through said dental arch structures to pass through said slot for activation of film carried by said film holder assembly, said machine including means for controllably continuously moving said film in said film holder assembly past said slot at a controlled rate of speed and other means for orbiting said slot and said film holder assembly about said dental arch structures of said patient, the combination therewith of the improvement thereto comprising intraoral container means containing a radiation source, pulley and lever means for effecting arcuate travel of said container means from one side of oral cavity of said patient to other side, said container means having an opening therein for passing radiation emitted by said radiation source therethrough while said container means rotatably scans said dental arch structures while disposed in oral cavity of said patient during said arcuate travel, additional means cooperating with said other means for rotating said pulley and lever means for maintaining said opening in constant collimated alignment with said slot as said slot and film holder assembly orbit said patient whereby said radiation passing through said container means during said arcuate travel within said oral cavity and entering said slot continuously activates said film to provide said panoramic radiograph.

2. The apparatus of claim 1 wherein said opening comprises a vertical slit of sufficient length to insure radiation passing therethrough from said radiation source enters substantial length of said slot and of sufficient width to provide an adequate focal trough.

3. The apparatus of claim 2 wherein said radiation source is a radioactive material selected from the group consisting of iodine 125, iron 55, and americium 241.

4. The apparatus of claim 3 wherein said radioactive source is iodine 125.

5. The apparatus of claim 3 wherein said radioactive source is iron 55.

6. The apparatus of claim 3 wherein said radioactive source is americium 241.

7. The apparatus of claim 1 wherein said additional means is a flexible shaft.

8. The apparatus of claim 1 wherein said pulley and lever means comprises
a hollow bar, a hollow flared portion affixed to an end of said hollow bar for insertion within said oral cavity of said patient, a first pulley rotatably mounted at a forward portion within said bar, a second pulley rotatably mounted within said flared portion, said container being disposed above said flared portion, means articulating between said second pulley and said container, a flexible shaft connected between said other means and said first pulley for rotating said first pulley in accordance with orbital movement of said film holder assembly whereby wire means communicating between said pulleys causes second pulley to rotate in a direction opposing direction of rotation of said first pulley.

9. The apparatus of claim 8 wherein said hollow bar is a C-shaped bar.

10. The apparatus of claim 8 wherein said bar is adjustable horizontally and vertically.

11. The apparatus of claim 8 wherein said means articulating between said second pulley and said container is a lever arm which rotates in accordance with rotation of said second pulley.

12. The apparatus of claims 8 or 10 wherein an arcuate slideway is provided in an upper surface of said flared portion for guiding said arcuate travel of said container means.

* * * * *